United States Patent
O'Brien et al.

(10) Patent No.: US 7,799,043 B2
(45) Date of Patent: Sep. 21, 2010

(54) CUTTING BALLOON HAVING SHEATHED INCISING ELEMENTS

(75) Inventors: Dennis O'Brien, Oceanside, CA (US); Carl Yee, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1828 days.

(21) Appl. No.: 10/725,178

(22) Filed: Dec. 1, 2003

(65) Prior Publication Data

US 2005/0119678 A1 Jun. 2, 2005

(51) Int. Cl.
*A61B 17/22* (2006.01)
*A61B 17/32* (2006.01)
*A61M 29/00* (2006.01)

(52) U.S. Cl. .................................................. 606/159
(58) Field of Classification Search ................. 606/159, 606/170, 191–192
See application file for complete search history.

(56) References Cited

U.S. PATENT DOCUMENTS

| | | | |
|---|---|---|---|
| 4,710,181 A | 12/1987 | Fuqua | |
| 4,738,666 A | 4/1988 | Fuqua | |
| 4,867,157 A | 9/1989 | McGurk-Burleson et al. | |
| 4,887,613 A | 12/1989 | Farr et al. | |
| 4,986,807 A | 1/1991 | Farr | |
| 5,030,201 A | 7/1991 | Palestrant | |
| 5,053,044 A | 10/1991 | Mueller et al. | |
| 5,071,424 A | 12/1991 | Reger | |
| 5,074,871 A | 12/1991 | Groshong | |
| 5,116,318 A | 5/1992 | Hillstead | |
| 5,156,610 A | 10/1992 | Reger | |
| 5,176,693 A | 1/1993 | Pannek, Jr. | |
| 5,178,625 A | 1/1993 | Groshong | |
| 5,196,024 A | 3/1993 | Barath | |
| 5,209,799 A | 5/1993 | Vigil | |
| 5,217,474 A | 6/1993 | Zacca et al. | |
| 5,226,909 A | 7/1993 | Evans et al. | |
| 5,282,484 A | 2/1994 | Reger | |
| 5,320,634 A * | 6/1994 | Vigil et al. | 606/159 |
| 5,372,601 A | 12/1994 | Lary | |

(Continued)

FOREIGN PATENT DOCUMENTS

JP 5293176 A 11/1993

(Continued)

*Primary Examiner*—Todd E Manahan
*Assistant Examiner*—Diane Yabut
(74) *Attorney, Agent, or Firm*—Crompton, Seager & Tufte LLC.

(57) ABSTRACT

A cutting balloon for use in a PTCA atherectomy procedure includes an elongated balloon that defines a longitudinal axis and is inflatable from a first deflated configuration to a second radially expanded configuration. One or more incising elements are mounted on the inflatable balloon. Compressible sheaths made of a relatively low durometer, flexible material are mounted on the balloon to protect the operative cutting surface of a respective incising element during assembly of the cutting balloon and transit of the cutting balloon to the treatment site. Each sheath extends farther from the longitudinal axis than the corresponding incising element and makes first contact with the tissue during a balloon inflation. Once contact has been established between the tissue and the sheath, further balloon inflation causes the sheath to radially compress between the tissue and the inflatable balloon exposing the operative cutting surface for tissue incision.

22 Claims, 5 Drawing Sheets

U.S. PATENT DOCUMENTS

| | | |
|---|---|---|
| 5,403,334 A | 4/1995 | Evans et al. |
| 5,556,405 A | 9/1996 | Lary |
| 5,616,149 A * | 4/1997 | Barath .................. 606/159 |
| 5,697,944 A | 12/1997 | Lary |
| 5,713,913 A | 2/1998 | Lary et al. |
| 5,728,123 A | 3/1998 | Lemelson et al. |
| 5,792,158 A | 8/1998 | Lary |
| 5,797,935 A | 8/1998 | Barath |
| 5,843,027 A | 12/1998 | Stone et al. |
| 5,865,844 A | 2/1999 | Plaia et al. |
| 5,919,200 A | 7/1999 | Stambaugh et al. |
| 6,027,514 A | 2/2000 | Stine et al. |
| 6,090,135 A | 7/2000 | Plaia et al. |
| 6,110,192 A | 8/2000 | Ravenscroft et al. |
| 6,258,108 B1 | 7/2001 | Lary |
| 6,306,151 B1 | 10/2001 | Lary |
| 6,416,527 B1 | 7/2002 | Berg et al. |
| 6,488,693 B2 | 12/2002 | Gannoe et al. |
| 6,632,231 B2 | 10/2003 | Radisch, Jr. |
| 6,730,105 B2 * | 5/2004 | Shiber .................. 606/159 |
| 7,494,497 B2 | 2/2009 | Weber |
| 2002/0151924 A1 | 10/2002 | Shiber |
| 2004/0034384 A1 | 2/2004 | Fukaya |
| 2004/0133223 A1 | 7/2004 | Weber |

FOREIGN PATENT DOCUMENTS

| | | |
|---|---|---|
| WO | 03011152 A1 | 2/2003 |
| WO | 03013642 A1 | 2/2003 |
| WO | 2004060460 A2 | 7/2004 |

* cited by examiner

CUTTING BALLOON HAVING SHEATHED INCISING ELEMENTS

FIELD OF THE INVENTION

The present invention pertains generally to medical devices. More particularly, the present invention pertains to cutting balloon catheters for revascularization of coronary and peripheral vessels. The present invention is particularly, but not exclusively, useful as a cutting balloon having incising elements that are shielded when the balloon is deflated.

BACKGROUND OF THE INVENTION

Although conventional percutaneous transluminal coronary angioplasty (PTCA) procedures have been somewhat effective in treating coronary artery disease, cutting balloons are currently viewed by many as the next generation treatment option for the revascularization of both coronary and peripheral vessels. The cutting balloon mechanism is unique in that the balloon pressure is distributed over one or more incising elements (e.g. microtomes). The incising elements function as stress concentrators and cut initiators in PTCA atherectomy procedures. Consequently, PTCA atherectomy procedures have been proven to minimize vessel recoil, lessen vessel injury and lower the rate of restenosis, as compared to conventional PTCA procedures.

The incising elements used in cutting balloons include an operative surface feature (e.g. edge) that is capable of incising tissue. In the absence of suitable precautions, the incising elements can tear, cut or perforate the thin, fragile inflation balloon during assembly of the cutting balloon, handling or during clinical use. In a worst case, a balloon perforation or tear can result in an unsuccessful PTCA atherectomy procedure and the loss of inflation fluid into the patient's vasculature. In addition to balloon perforation concerns, another consideration involves the prevention of an inadvertent or unwanted cutting or incising of tissue as the cutting balloon is either being advanced into or withdrawn from the vasculature.

Along these lines, a device having a parting edge which is shielded within the pleats of an expandable clover leaf shaped tube is disclosed by Shiber in U.S. patent application Publication No. US 2002/0151924, filed Oct. 17, 2002 and entitled "Clover Leaf Shaped Tubular Medical Device". However, the clover leaf design disclosed by Shiber does not necessarily protect the relatively fragile balloon during installation of the parting edges on the clover leaf balloon. In addition, because the parting edges are located within the pleats of the balloon, portions of the balloon may be exposed to the parting edges when the device is twisted, turned and bent through the curved vasculature of a patient.

In light of the above, it is an object of the present invention to provide a protective sheath for an incising element mounted on an inflatable balloon which compresses to expose the incising element during balloon inflation at a treatment site. Another object of the present invention is to provide a protective sheath for an incising element mounted on an inflatable balloon that protects the incising element from inadvertently cutting tissue as the deflated balloon is maneuvered through the vasculature of a patent. Still another object of the present invention is to provide a protective sheath for an incising element mounted on an inflatable balloon that is easy to use, relatively simple to manufacture and comparatively cost effective.

SUMMARY OF THE INVENTION

The present invention is directed to a cutting balloon which in one application can be used on a medical catheter to incise and dilate stenotic tissue at a treatment site in a body vessel of a patient. A typical cutting balloon includes an elongated balloon that defines a longitudinal axis and is inflatable from a first deflated configuration to a second radially expanded configuration.

The cutting balloon further includes one or more rigid, elongated incising elements which could be, for example, a blade, a round wire or a hardened polymer. The incising elements are typically oriented longitudinally and mounted on the inflatable balloon. Specifically, when the inflatable balloon is in the radially expanded configuration, each incising element extends radially from the surface of the inflatable balloon to an operative surface feature (e.g. edge) that is capable of incising tissue. The cutting balloon may further include one or more mounting pads, with each mounting pad holding a respective incising element. For example, each incising element may be partially encapsulated in a respective mounting pad which, in turn, is adhesively bonded to the outer surface of the inflatable balloon.

For the present invention, the cutting balloon includes one or more compressible sheaths that are made of a relatively low durometer, flexible material. Functionally, each sheath is provided to protect the operative surface feature of a respective incising element during assembly of the cutting balloon and transit of the cutting balloon to the treatment site. In greater structural detail, each sheath may include a pair of elongated sheath members that are oriented longitudinally and attached to the mounting pad to interpose an incising element between the pair of sheath members. In one embodiment, each sheath has a single sheath member.

Each sheath member extends radially from the mounting pad and terminates at a sheath member surface that is located farther from the longitudinal axis than the operative surface feature of the corresponding incising element. With this cooperation of structure, the sheath member(s) makes first contact with the tissue during a balloon inflation. Once contact has been established between the tissue and the sheath members, further inflation of the inflatable balloon causes the sheath member(s) to radially compress, and in some cases deflect, between the tissue and the inflatable balloon exposing the operative surface feature of the incising element for tissue incision. In one aspect of the present invention, the sheath members can be configured to selectively limit the amount of incising element that is exposed, and as a consequence, control the incision depth.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
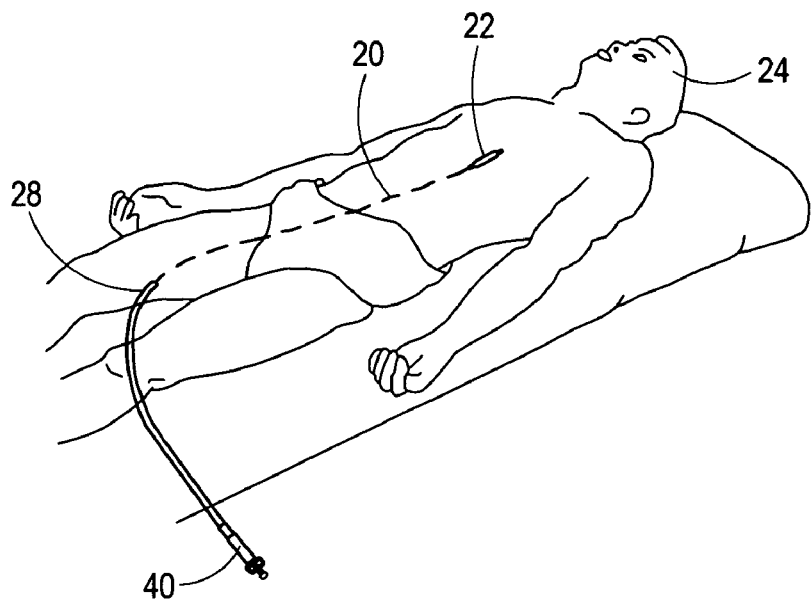
FIG. 1 is a simplified, perspective view of a catheter having a cutting balloon operationally positioned in the upper body of a patient.

Referring initially to FIG. 1, a catheter 20 having a cutting balloon 22 is shown for performing a medical procedure at an internal treatment site of a patient 24. More specifically, the catheter 20 is shown positioned to treat a lesion in an upper body artery. Although the catheter 20 is capable of performing a medical procedure in an upper body artery such as a coronary artery, those skilled in the pertinent art will quickly recognize that the use of the catheter 20 as herein described is not limited to use in a specific artery, but, instead can be used in vascular conduits and other ductal systems throughout the human body.

Figure 2:
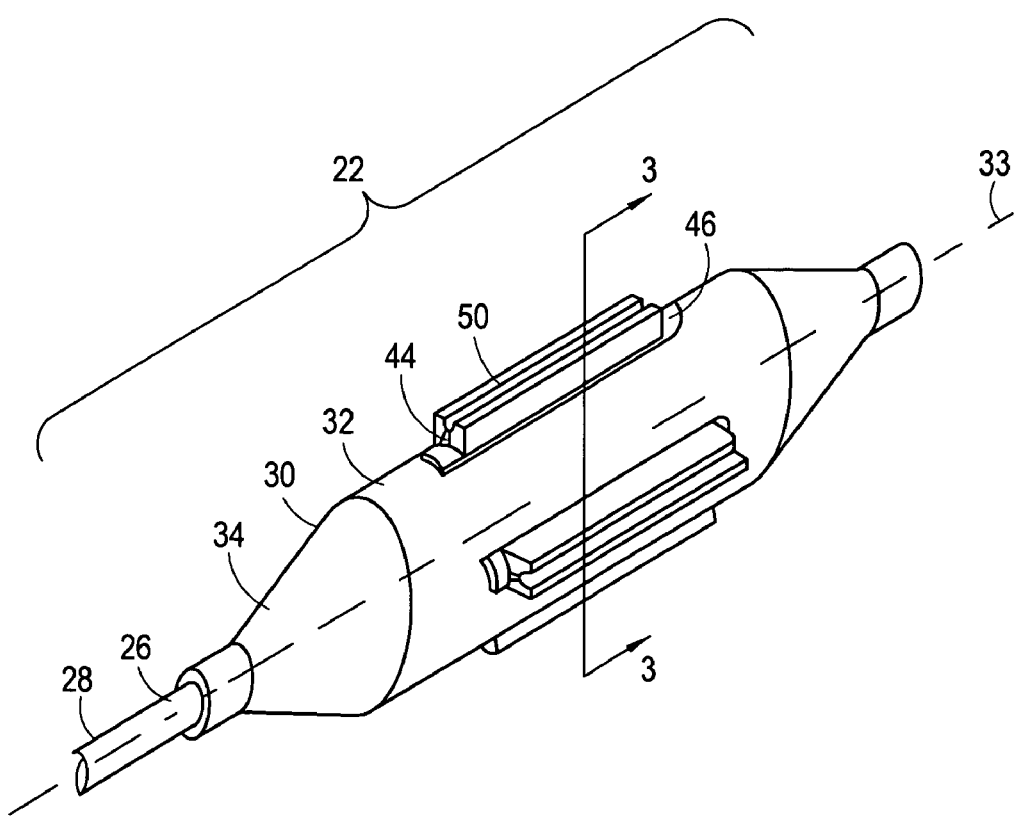
FIG. 2 is an enlarged, perspective view of a cutting balloon.
Figure 3:
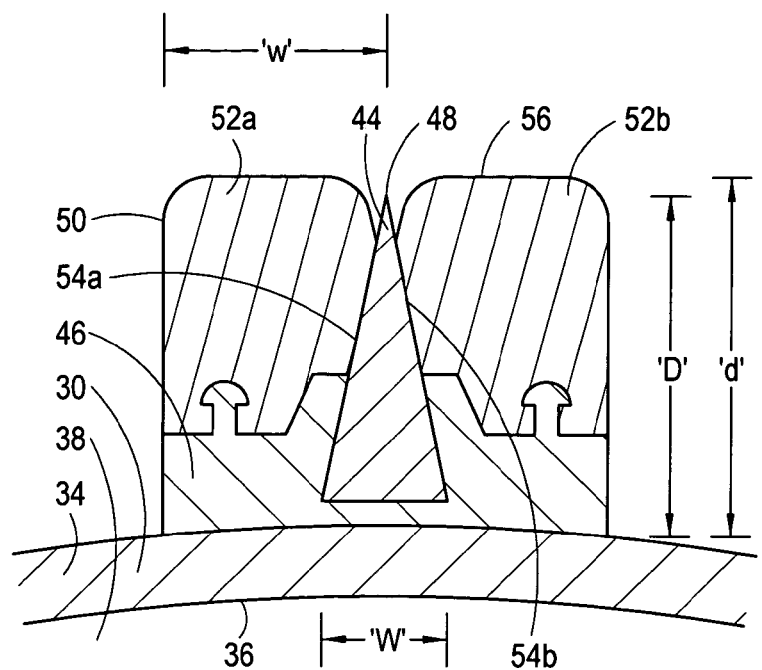
FIG. 3 is a partial, cross-sectional view of the cutting balloon shown in FIG. 2 as seen along line 3-3 in FIG. 2.

Referring now to FIG. 2, the distal portion of the catheter 20 is shown to include a cutting balloon 22 that is attached to the distal end 26 of an inflation tube 28. FIG. 2 further shows that the cutting balloon 22 can include an inflatable balloon 30 that typically includes a cylindrical shaped working section 32 that defines an axis 33. Typically, the inflatable balloon 30 is made of a polymeric material such as polyethylene terephthalate (PET) or nylon. As best seen in FIG. 3, the inflatable balloon 30 can be characterized as having an outer surface 34 and an opposed inner surface 36 that surrounds an inflation volume 38 that can be infused with a medical grade fluid to expand the inflatable balloon 30. More specifically, as shown in FIG. 1, an inflation device, which for the embodiment shown is a syringe 40, can be activated to pump a medical grade fluid through the inflation tube 28 to expand the inflatable balloon 30.

Cross-referencing FIGS. 2 and 3, it can be seen that the cutting balloon 22 further includes a plurality of incising elements, which in this case is four elongated cutting blades 44. For the embodiment shown, the four longitudinally aligned blades 44 are uniformly distributed around the circumference of the working section 32 of the inflatable balloon 30. Typically, each blade 44 is made of a medical grade metal such as stainless steel. As best seen in FIG. 3, a portion of each blade 44 is encapsulated in a respective mounting pad 46, thereby affixing the blade 44 to the respective mounting pad 46. Typically, each mounting pad 46 is made of a relatively flexible polymeric material such as polyurethane and is bonded (e.g. heat bonded or adhesively bonded) to the outer surface 34 of the inflatable balloon 30. It can further be seen that each blade 44 extends from the mounting pad 46 to an operative surface feature that is capable of incising tissue, which in this case is a cutting edge 48.

Continuing with cross-reference to FIGS. 2 and 3, it can be seen that the cutting balloon 22 includes one or more compressible sheaths 50 (typically one sheath 50 for each blade 44) that are made of a relatively low durometer, compressible material. As further shown, each sheath 50 may include a pair of elongated sheath members 52a,b that are each oriented longitudinally and attached to a mounting pad 46. The attachment between the sheath members 52a,b and mounting pad 46 can be a mechanical attachment as shown, or the sheath members 52a,b can be bonded (e.g. heat bonded or adhesively bonded) to the mounting pad 46. In some cases, sheath members 52a,b can be bonded directly to the balloon 30. In addition, the sheath members 52a,b can be bonded to the sides 54a,b of the blade 44. Also shown, each sheath member 52a,b is positioned alongside a blade 44 to interpose the blade 44 between the sheath members 52a,b.

It can be further seen that each sheath member 52 extends radially from the mounting pad 46 and terminates at a surface 56 that is located farther from the longitudinal axis 33 than the cutting edge 48 of the corresponding blade 44. Specifically, as shown, each sheath member 52 extends a radial distance, 'd' from the outer surface 34 of the balloon 30 (when the sheath is uncompressed) and the blade 44 extends a distance 'D' from the outer surface 34 of the inflatable balloon 30, with 'd'>'D'.

For the embodiment shown in FIG. 3, each sheath member 52 has an azimuthal width 'w' that is greater than twice the azimuthal width 'W' of the blade 44 measured where the blade 44 extends from the mounting pad 46 (i.e. 'w'>2W). This geometry encourages radial compression of the sheath member 52 instead of azimuthal deflection which may be problematic, for example, when anatomical features of the vessel or lesion prevent deflection of a deflecting sheath.

Figure 4:
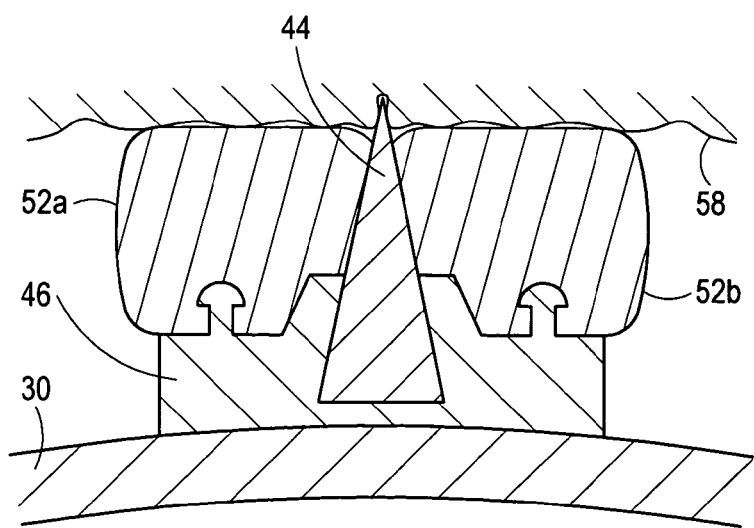
FIG. 4 is a partial, cross-sectional view of the cutting balloon as in FIG. 3, shown after the balloon has been inflated to expose a cutting blade and incise tissue.

The functionality of the sheath 50 can perhaps best be appreciated with cross-reference to FIGS. 3 and 4. As shown in FIG. 3, the sheath 50 is configured to protect the cutting edge 48 of blade 44 during assembly of the cutting balloon 22 and transit of the cutting balloon 22 to the treatment site. On the other hand, once the cutting balloon 22 is positioned at the treatment site and expanded, the sheath members 52a,b make first contact with the tissue 58 (see FIG. 4). Once contact has been established between the tissue 58 and the sheath members 52a,b, further inflation of the inflatable balloon 30 causes the sheath members 52a,b to radially compress, and in some cases deflect, between the tissue 58 and the inflatable balloon 30 exposing the cutting edge 48 for tissue incision.

For the embodiment shown in FIGS. 3 and 4, the sheath members 52a,b are bonded to the sides 54a,b of the blade 44. As shown, this structure limits the amount of cutting blade 44 that is exposed to the portion of the cutting blade 44 that is not bonded to the sheath members 52a,b. As a consequence, the incision depth is limited to the exposed portion of the cutting blade 44.

Figure 5:
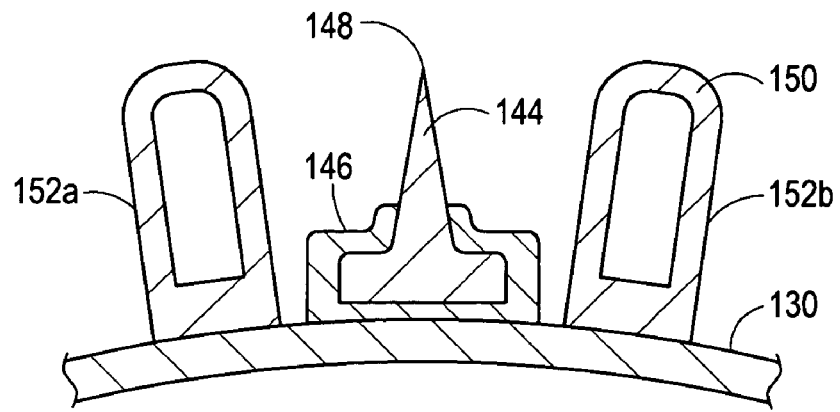
FIG. 5 is a partial, cross-sectional view as in FIG. 3 showing an alternate embodiment of a cutting balloon.
Figure 6:
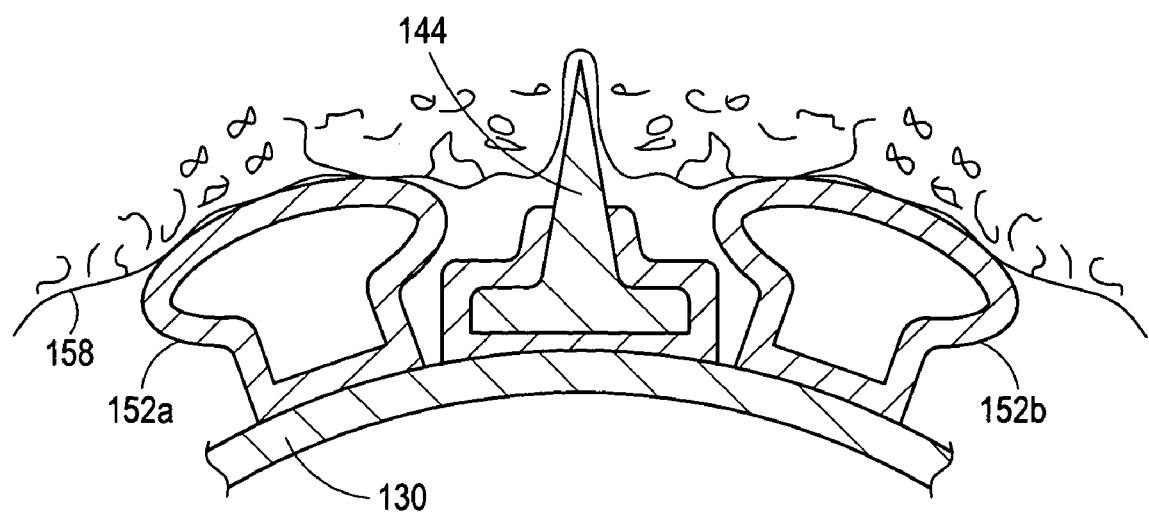
FIG. 6 is a partial, cross-sectional view of the cutting balloon as in FIG. 5, shown after the balloon has been inflated to expose a cutting blade and incise tissue.

FIGS. 5 and 6 show an alternate embodiment of a sheath (designated 150) having a pair of sheath members 152a,b that are each shaped as a hollow, elongated tube. The tube-shaped sheath members 152a,b are positioned longitudinally on balloon 130 to interpose the blade 144 (which is partially encapsulated in mounting pad 146) between said sheath members 152a,b. As shown in FIG. 6, each sheath member 152a,b is made of a flexible material and radially compresses between tissue 158 and the balloon 130 to expose the cutting edge 148 of the blade 144 for tissue incision during an inflation of the balloon 130.

Figure 7:
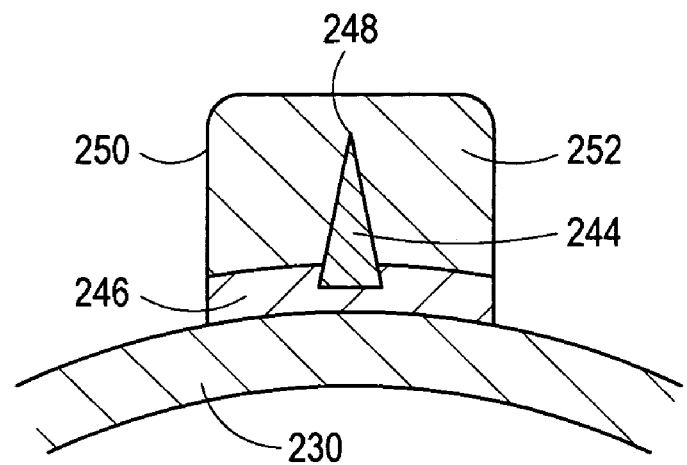
FIG. 7 is a partial, cross-sectional view as in FIG. 3 showing another alternate embodiment of a cutting balloon.
Figure 8:
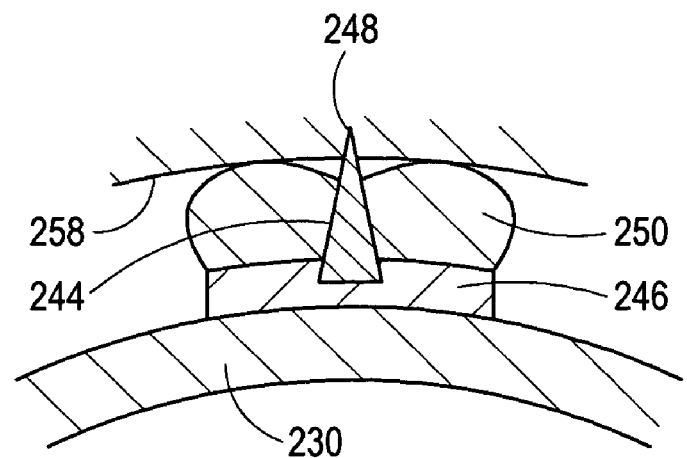
FIG. 8 is a partial, cross-sectional view of the cutting balloon as in FIG. 5, shown after the balloon has been inflated to expose a cutting blade and incise tissue.

FIGS. 7 and 8 show an alternate embodiment of a sheath (designated 250) having a single sheath member 252 which is attached to a mounting pad 246. A portion of a blade 244 is embedded in the mounting pad 246, which in turn, is attached to the balloon 230. In this embodiment, the cutting edge 248 of the blade 244 is embedded in the sheath 250 when the balloon 230 is initially in the first configuration, as shown in FIG. 7. As shown in FIG. 6, the sheath member 252 is made of a compressible material and radially compresses between tissue 258 and the balloon 230 during inflation of the balloon 230. During this compression, the cutting edge 248 cuts through the sheath member 252 to expose the cutting edge 248 of the blade 244. Once the cutting edge 248 is exposed, continued inflation of the balloon 230 drives the exposed cutting edge 248 into the tissue 258, to incise the tissue 258, as shown in FIG. 8.

Figure 9:
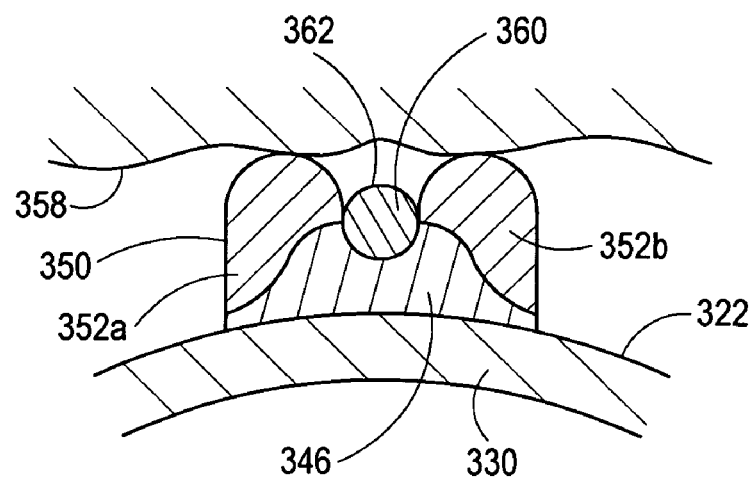
FIG. 9 is a partial, cross-sectional view as in FIG. 3 showing another alternate embodiment of a cutting balloon wherein the incising element is a round wire.
Figure 10:
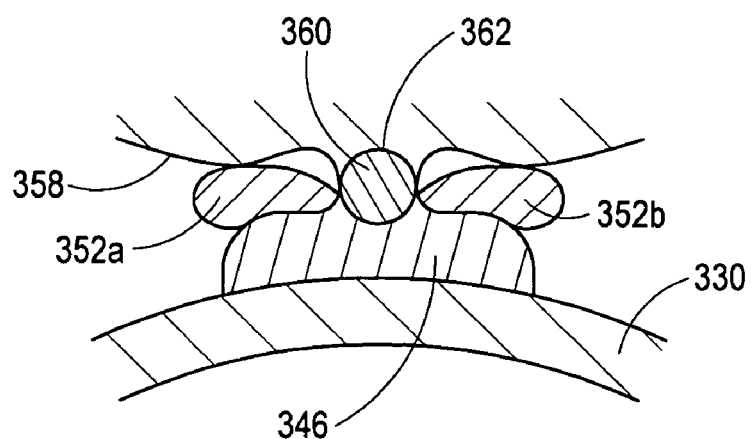
FIG. 10 is a partial, cross-sectional view of the cutting balloon as in FIG. 9 shown after the balloon has been inflated to expose an operative cutting surface and incise tissue.

FIGS. 9 and 10 show an alternate embodiment of a cutting balloon 322 having an incising element that is formed as a round wire 360 having an operative cutting surface 362. The cutting balloon 322 includes a sheath 350 having sheath members 352a,b which are attached to a mounting pad 346. A portion of a round wire 360 is embedded in the mounting pad 346, which in turn, is attached to the balloon 330. As shown in FIG. 10, the sheath members 352a,b are made of a compressible material and radially compress between tissue 358 and the balloon 330 during inflation of the balloon 330. During this compression, the operative cutting surface 362 is exposed and continued inflation of the balloon 330 drives the operative cutting surface 362 into the tissue 358, to incise the tissue 358, as shown in FIG. 10.

While the particular cutting balloon having sheathed incising elements as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A cutting balloon for use on a medical catheter to incise tissue at a treatment site in a body vessel of a patient, said cutting balloon comprising:
    an elongated balloon defining a longitudinal axis, said balloon being inflatable from a first deflated configuration to a second radially expanded configuration;
    an elongated incising element mounted on said balloon and oriented longitudinally, said incising element having a length and extending radially from said balloon to an operative surface feature capable of incising tissue; and
    a radially compressible sheath mounted on said balloon along the length of said incising element and extending radially from said balloon and beyond said surface feature when said balloon is in the first configuration to protect said surface feature during transit to the treatment site, said sheath being positioned for radial compression between said tissue and said balloon to expose said surface feature for tissue incision when said balloon is inflated into the second configuration.

2. The cutting balloon as recited in claim 1 further comprising a mounting pad for attaching said incising element to said balloon.

3. The cutting balloon as recited in claim 2 wherein said incising element is partially encapsulated in said mounting pad and said mounting pad is bonded to said balloon.

4. The cutting balloon as recited in claim 2 wherein said sheath is attached to said mounting pad.

5. The cutting balloon as recited in claim 1 wherein each said sheath member extends a radial distance, d, from said balloon when uncompressed and said incising element extends a distance, D, from said balloon, with d>D.

6. The cutting balloon as recited in claim 1 wherein said incising element is a blade and said surface feature is a cutting edge.

7. The cutting balloon as recited in claim 6 wherein said blade is partially encapsulated in a mounting pad, said mounting pad is bonded to said balloon, each said sheath member has an azimuthal width w, and wherein said blade has an azimuthal width, W, where said blade extends from said mounting pad, with w>2W.

8. The cutting balloon as recited in claim 6 wherein said cutting edge of said blade is embedded in said sheath when said balloon is initially in said first configuration, said cutting edge oriented relative to said balloon to cut through said sheath for exposure of said cutting edge to incise tissue during radial compression of said sheath.

9. The cutting balloon as recited in claim 1 wherein said incising element is a round wire.

10. The cutting balloon as recited in claim 1 wherein said incising element is made of a hardened polymer.

11. The cutting balloon as recited in claim 1 wherein said sheath is made of a low durometer material.

12. The cutting balloon as recited in claim 1 wherein said sheath is made of a porous polyurethane material.

13. A cutting balloon for use on a medical catheter to incise tissue at a treatment site in a body vessel of a patient, said cutting balloon comprising:
    an elongated balloon defining a longitudinal axis, said balloon being inflatable from a first deflated configuration to a second radially expanded configuration;
    an elongated cutting blade mounted on said balloon and oriented longitudinally, said blade extending radially from said balloon to a cutting edge when said balloon is in said second configuration; and
    a sheath for protecting said cutting edge during transit to the treatment site, said sheath having a pair of sheath members with each sheath member being shaped as a hollow, elongated tube and positioned longitudinally on said balloon to interpose said blade between said sheath members, each said sheath member made of a flexible material to radially compress between said tissue and said balloon to expose said cutting edge for tissue incision during an inflation of said balloon.

14. The cutting balloon as recited in claim 13 further comprising a mounting pad for attaching said blade to said balloon.

15. The cutting balloon as recited in claim 14 wherein said blade is partially encapsulated in said mounting pad, said sheath is attached to said mounting pad, and said mounting pad is bonded to said balloon.

16. The cutting balloon as recited in claim 13 wherein each said sheath member extends a radial distance, d, from said balloon when uncompressed and said blade extends a distance, D, from said balloon, with d>D.

17. The cutting balloon as recited in claim 13 wherein each said sheath member is substantially rectangular shaped in a plane normal to said direction of tube elongation.

18. A cutting balloon for use on a medical catheter to incise tissue at a treatment site in a body vessel of a patient, said cutting balloon comprising:
    an elongated balloon defining a longitudinal axis, said balloon being inflatable from a first deflated configuration to a second radially expanded configuration;
    an elongated cutting blade mounted on said balloon and oriented longitudinally, said blade extending radially from said balloon to a cutting edge when said balloon is in said second configuration; and a sheath for protecting said cutting edge during transit to the treatment site, said sheath having a pair of elongated sheath members with each sheath member being mounted longitudinally on said balloon and shaped to expose a preselected portion of said cutting blade for tissue incision when said sheath members are radially compressed between said tissue and said balloon during an inflation of said balloon.

19. The cutting balloon as recited in claim 18 wherein said blade has a first side and a second side and each said sheath member is in contact with a portion of a respective side to define said pre-selected exposed portion of said cutting blade.

20. The cutting balloon as recited in claim 19 wherein said blade is partially encapsulated in said mounting pad, said sheath is attached to said mounting pad, and said mounting pad is bonded to said balloon.

21. The cutting balloon as recited in claim 18 further comprising a mounting pad for attaching said blade to said balloon.

22. The cutting balloon as recited in claim 18 wherein each said sheath member extends a radial distance, d, from said balloon when uncompressed and said blade extends a distance, D, from said balloon, with d>D.

* * * * *